US009774166B2

(12) United States Patent
Jayaraman et al.

(10) Patent No.: US 9,774,166 B2
(45) Date of Patent: Sep. 26, 2017

(54) WIDELY TUNABLE SWEPT SOURCE

(71) Applicants: Praevium Research, Inc., Santa Barbara, CA (US); Thorlabs, Inc., Newton, NJ (US)

(72) Inventors: Vijaysekhar Jayaraman, Goleta, CA (US); Christopher Burgner, Santa Barbara, CA (US); Demis John, Goleta, CA (US); Peter Heim, Jessup, MD (US); Alex Ezra Cable, Newton, NJ (US)

(73) Assignees: Praevium Research, Inc., Sanata Barbara, CA (US); Thorlabs, Inc., Newton, NJ (US)

( * ) Notice: Subject to any disclaimer, the term of this patent is extended or adjusted under 35 U.S.C. 154(b) by 585 days.

(21) Appl. No.: 14/214,201

(22) Filed: Mar. 14, 2014

(65) Prior Publication Data

US 2014/0268169 A1    Sep. 18, 2014

Related U.S. Application Data

(60) Provisional application No. 61/793,730, filed on Mar. 15, 2013.

(51) Int. Cl.
*H01S 5/183* (2006.01)
*H01S 5/30* (2006.01)
*H01S 5/20* (2006.01)

(52) U.S. Cl.
CPC ...... *H01S 5/18366* (2013.01); *H01S 5/18308* (2013.01); *H01S 5/18311* (2013.01); *H01S 5/18341* (2013.01); *H01S 5/18369* (2013.01); *H01S 5/18372* (2013.01);

(Continued)

(58) Field of Classification Search
CPC ............ H01S 5/18366; H01S 5/18341; H01S 5/3095; H01S 5/18369; H01S 5/2059; H01S 5/18372; H01S 5/18308; H01S 5/18311; H01S 5/18377
See application file for complete search history.

(56) References Cited

U.S. PATENT DOCUMENTS

| 5,754,578 A | 5/1998 | Jayaraman |
| 6,227,724 B1 | 5/2001 | Verdiell |
| 6,741,629 B1 | 5/2004 | Garnache et al. |

(Continued)

FOREIGN PATENT DOCUMENTS

| EP | 2133686 A1 | 12/2009 |
| WO | 2005122349 A1 | 12/2005 |
| WO | 2011121962 A1 | 10/2011 |

OTHER PUBLICATIONS

International Search Report mailed Sep. 18, 2014 in corresponding International Application No. PCT/US2014/029458.

(Continued)

*Primary Examiner* — Xinning Niu
(74) *Attorney, Agent, or Firm* — Graham Curtin, P.A.

(57) ABSTRACT

A high-speed, single-mode, high power, reliable and manufacturable wavelength-tunable light source operative to emit wavelength tunable radiation over a wavelength range contained in a wavelength span between about 950 nm and about 1150 nm, including a vertical cavity laser (VCL), the VCL having a gain region with at least one compressively strained quantum well containing Indium, Gallium, and Arsenic.

30 Claims, 10 Drawing Sheets

(52) U.S. Cl.
CPC ......... *H01S 5/18377* (2013.01); *H01S 5/2059* (2013.01); *H01S 5/3095* (2013.01)

(56) References Cited

U.S. PATENT DOCUMENTS

| | | | |
|---|---|---|---|
| 8,263,426 B2* | 9/2012 | Ko | G01H 11/06 257/415 |
| 2002/0031155 A1* | 3/2002 | Tayebati | G01J 3/26 372/50.1 |
| 2002/0074631 A1 | 6/2002 | Sato et al. | |
| 2002/0126725 A1 | 9/2002 | Tayebati | |
| 2002/0131458 A1* | 9/2002 | Sirbu | B82Y 20/00 372/20 |
| 2003/0031221 A1 | 2/2003 | Wang | |
| 2003/0169786 A1 | 9/2003 | Kapon et al. | |
| 2006/0245456 A1* | 11/2006 | Lasri | H01S 3/06791 372/18 |
| 2007/0183643 A1 | 8/2007 | Jayaraman | |
| 2007/0223546 A1* | 9/2007 | Brenner | B82Y 20/00 372/43.01 |
| 2009/0059970 A1* | 3/2009 | Atia | G01N 21/4795 372/20 |
| 2010/0282005 A1* | 11/2010 | Kwon | G01G 3/13 73/865 |
| 2011/0261849 A1 | 10/2011 | Shinagawa et al. | |
| 2012/0162659 A1 | 6/2012 | Goldberg | |
| 2013/0016360 A1 | 1/2013 | Ensher et al. | |

OTHER PUBLICATIONS

Grulkowski et al., "Retinal, anterior segment and full eye imaging using ultrahigh speed swept source OCT with vertical-cavity surface emitting lasers", Biomedical Optics Express, Nov. 1, 2012 / pp. 2733-51/ vol. 3, No. 11.

Grulkowski Ireneusz et al:, "Retinal, anterior segment and full eye imaging using ultrahigh speed swept source OCT with vertical-cavity surface emitting lasers", Biomedical Optics Express, Nov. 1, 2012 / pp. 2733-2751/ vol. 3, No. 11.

Jayaraman V et al: "Rapidly swept, ultra-widely-tunable 1060 nm MEMS-VCSELs", Electronics Letters, IEE Stevenage, GB, vol. 48, No. 21, Oct. 11, 2012, ISSN: 0013-5194.

Partial Supplementary European Search Report dated Nov. 4, 2016, issued for corresponding European Patent Application No. 14 763 284.8.

* cited by examiner

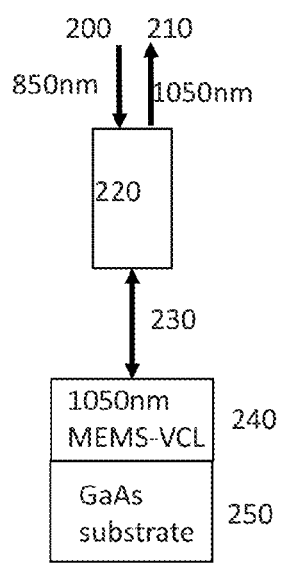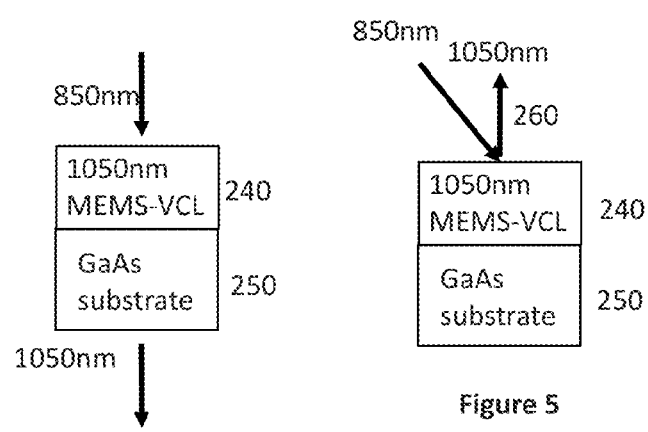
Figure 3
Figure 4
Figure 5

US 9,774,166 B2

WIDELY TUNABLE SWEPT SOURCE

CROSS REFERENCES TO RELATED APPLICATIONS

This application claims the benefit of U.S. Provisional Patent Application No. 61/793,730 filed on Mar. 15, 2013. The disclosure of U.S. Provisional Patent Application 61/793,730 is hereby incorporated by reference.

STATEMENT REGARDING FEDERALLY SPONSORED RESEARCH OR DEVELOPMENT

This invention was made under NIH grant R44CA101067 and R44EY022864. The U.S. government has certain rights in this invention.

FIELD OF THE INVENTION

This invention relates generally to optical coherence tomography and tunable lasers.

BACKGROUND

Optical coherence tomography (OCT) is a technique for high-resolution depth profiling of a sample below the sample surface. In recent years, swept source optical coherence tomography (SSOCT) systems have demonstrated superior imaging speed, imaging range, and image quality. The key technology element of SSOCT systems is the wavelength swept laser source. The MEMS-tunable vertical cavity laser (MEMS-VCL) has proven to be an important key wavelength-swept source for SS-OCT at 1300 nm and 1050 nm, as described, for example in (I. Grulkowski, J Liu, B. Potsaid, V. Jayaraman, C. D. Lu, J. Jiang, A. E. Cable, J. S. Duker, and J. G. Fujimoto, "Retinal, anterior segment, and full-eye imaging using ultra-high speed swept source OCT with vertical cavity surface-emitting lasers," *Biomedical Optics Express*, vol. 3, no. 11, pp. 2733-2751). For SS-OCT systems to be commercially viable, swept sources based on 1050 nm VCLs must provide substantially single longitudinal, transverse and polarization mode operation over a wide tuning range, be swept at hundreds of kHz rates for hundreds of billions of cycles, provide sufficient output power for SSOCT imaging, and be manufacturable and long-term reliable.

From the foregoing, it is clear that what is required is a MEMS-VCL at 1050 nm that meets tuning range, speed, coherence length, and output power requirements of SS-OCT systems, and is both manufacturable and long-term reliable.

SUMMARY OF THE INVENTION

The present invention provides several preferred and alternate manufacturable and reliable embodiments of a high-speed, single-mode, high power, reliable and manufacturable swept laser source based around a tunable 1050 nm VCL.

One embodiment provides a wavelength-tunable light source operative to emit wavelength tunable radiation over a wavelength range contained in a wavelength span between about 950 nm and about 1150 nm, the wavelength tunable light source including a vertical cavity laser (VCL), the VCL having a gain region with at least one compressively strained quantum well containing Indium, Gallium, and Arsenic, the vertical cavity laser further comprising a first portion including a first mirror, a second portion including a second mirror attached to a mechanical structure including a flexible membrane with a support structure, an adjustable airgap between the second portion and the first portion, a first means for injecting electrons and holes into the gain region, a second means for adjusting the airgap, and a third means for obtaining substantially single longitudinal and transverse mode operation over the wavelength tuning range, wherein a peak room-temperature photoluminescence wavelength of the gain region is more than about 20 nm shorter than a maximum operating wavelength of the tunable laser.

Another embodiment provides wavelength-tunable light source operative to emit wavelength tunable radiation over a wavelength range contained in a wavelength span between about 950 nm and about 1150 nm, the wavelength tunable light source including a vertical cavity laser (VCL), the VCL having a gain region with at least one compressively strained quantum well containing Indium, Gallium, and Arsenic, the vertical cavity laser further comprising a first portion including a first mirror, a second portion including a second mirror attached to a mechanical structure including a flexible membrane with a support structure, an adjustable airgap between the second portion and the first portion, a first means for injecting electrons and holes into the gain region, a second means for adjusting the airgap, and a vacuum environment surrounding the vertical cavity laser.

Another embodiment provides a wavelength-tunable light source operative to emit wavelength tunable radiation over a wavelength range contained in a wavelength span between about 950 nm and about 1150 nm, the wavelength tunable light source including a vertical cavity laser (VCL), the VCL having a gain region with at least one compressively strained quantum well containing Indium, Gallium, and Arsenic, the vertical cavity laser further comprising a first portion including a first mirror, a second portion including a second mirror attached to a mechanical structure including a flexible membrane with a support structure, an adjustable airgap between the second portion and the first portion, a first means for electrical injection of electrons and holes into the gain region, the first means including a tunnel junction, a second means for adjusting the airgap, and a third means for obtaining substantially single longitudinal and transverse mode operation over the wavelength tuning range.

Another embodiment provides a wavelength-tunable light source operative to emit wavelength tunable radiation over a wavelength range contained in a wavelength span between about 950 nm and about 1150 nm, the wavelength tunable light source including a vertical cavity laser (VCL), the VCL having a gain region with at least one compressively strained quantum well containing Indium, Gallium, and Arsenic, the vertical cavity laser further comprising a first portion including a first mirror, a second portion including a second mirror attached to a mechanical structure including a flexible membrane with a support structure, an adjustable airgap between the second portion and the first portion, a first means for injecting electrons and holes into the gain region, a second means for adjusting the airgap, and a third means for obtaining substantially single longitudinal and transverse mode operation over the wavelength tuning range, said wavelength tunable light source further comprising a semiconductor optical amplifier.

BRIEF DESCRIPTION OF THE DRAWINGS

FIG. 3 shows a device with WDM separation according to an embodiment.

FIG. 4 shows a bottom-emission device according to an embodiment.

FIG. 5 shows a device with off-axis pumping according to an embodiment.

DETAILED DESCRIPTION OF PREFERRED AND ALTERNATE EMBODIMENTS

Figure 1:
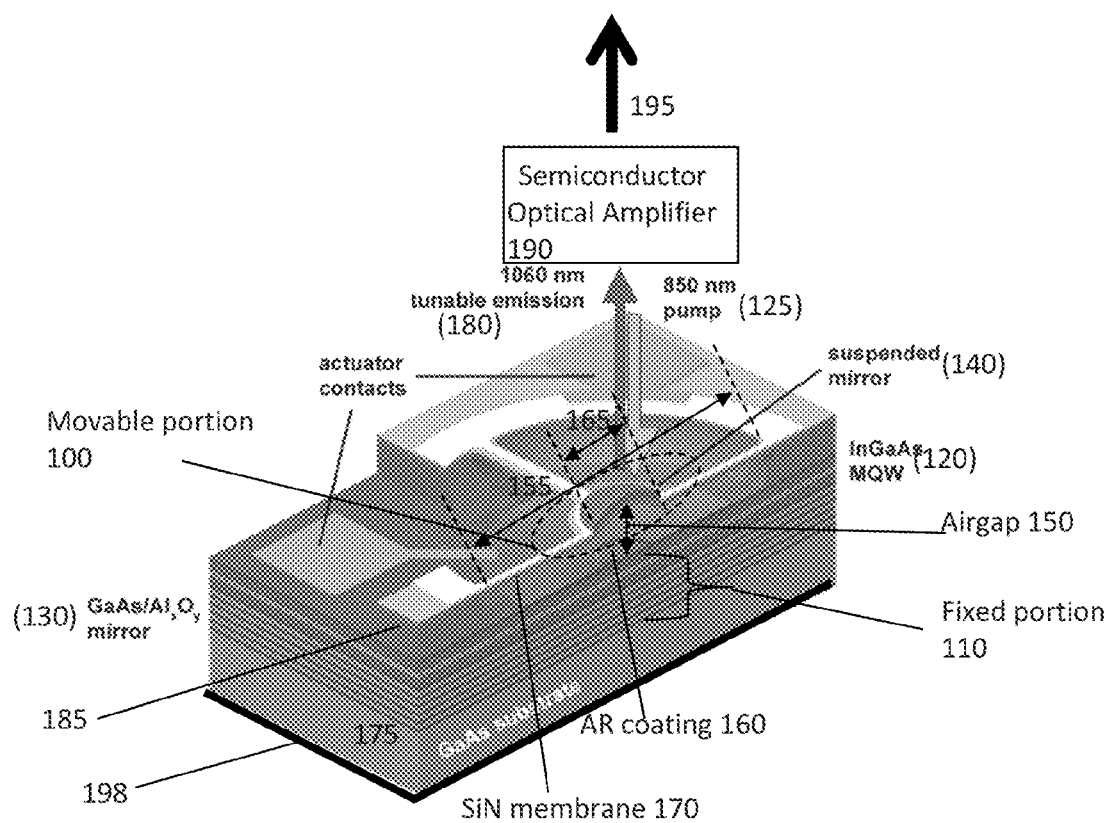
FIG. 1 is an optically pumped MEMS-VCL device according to an embodiment.

FIG. 1 shows a schematic of a preferred embodiment of a high performance, manufacturable, and reliable wavelength swept source according the present invention. The design of both the tuning mechanism and the gain medium will enable a mean time to failure of well over 1000 hours, where failure is defined as the point when either achievable tuning range or output power drops by 10% or more. For some applications, a shorter mean time to failure, such as 100 hours may be sufficient. This source emits wavelength-swept radiation over a wavelength tuning range contained in a range of about 950-1150 nm, with an average output power and a peak power wavelength. An optically pumped tunable MEMS-VCL includes a fixed first portion 110 and a movable second portion 100. Although the preferred tuning mechanism shown is a MEMS-tuning mechanism other tuning mechanisms such as electro-thermal actuation relying on an expanded membrane using resistive heating are possible. The first portion includes an InGaAs MQW gain region 120 with at least one and ideally 3 compressively strained indium gallium arsenide (InGaAs) quantum wells with GaAs barriers, which will absorb a pump radiation from an optically pumped laser source 125. The InGaAs quantum wells can comprise 2 quantum states for enhanced gain-bandwidth. The optically pumped laser source 125 has a wavelength in a range of about 750-870 nm wavelength, preferably at about 850 nm, and serves to inject electrons and holes into the gain region 120 to enable lasing. The first portion 110 also includes a bottom mirror 130, which is a fully oxidized GaAs/AlxOy mirror, formed by lateral oxidation of a GaAs/AlAs alternating stack. The lower refractive index portion of this mirror can be also formed by oxidation of Al(x)Ga(1−x)As, with x preferably >0.9. The high index portion also need not be GaAs and can be AlGaAs. The movable second portion 100 includes a top suspended dielectric mirror 140, separated by an airgap 150 from the first portion 110. An anti-reflection (AR) coating 160 at the interface between the first portion 110 and the airgap 150 suppresses unwanted reflections and widens laser tuning range. The dielectric mirror 140 is ideally formed by a quarter wave stack of silicon dioxide (SiO2) and tantalum pentoxide (Ta2O5), although the Ta2O5 could be replaced by an oxide of niobium, hafnium, titanium, by silicon, or by a number of other high index materials well-known to those skilled in the art of VCSEL design and fabrication. The dielectric mirror is also curved to provide a half-symmetric cavity, which promotes high power single-mode operation. The dielectric mirror sits on a membrane 170, which is preferably silicon nitride, and is supported on its ends by a support structure 185, which is preferably germanium. This support structure is ideally the same material used as a sacrificial layer to undercut the membrane 170. Other candidate materials for the support structure include silicon, polyimide, photoresist, or SU-8. The use of a silicon nitride membrane provides an extremely reliable membrane that can survive more than a trillion cycles of flexure, as required in many high-speed SS-OCT systems. The ideal support structure is one which can be undercut by a dry gas such as xenon diflouride or oxygen, instead of by a wet chemical etch. The undercut gas should not substantially etch other elements of the VCL structure. Use of a wet chemical etched sacrificial layer necessitates critical point drying, which complicates device processing, dicing, and packaging. For example, it is preferable to dice a processed wafer of VCLs into individual VCLs before undercutting the sacrificial layer since this enables the structure to remain robust for handling. Undercut of a sacrificial layer at the die level is very difficult if critical point drying is required.

The silicon nitride membrane 170 is ideally integral with the dielectric mirror, and actually forms the first layer of the dielectric mirror. In addition, a lateral extent 165 of the suspended dielectric mirror 140 is smaller than a lateral extent 155 of the membrane 170. This reduces the mass of the MEMS actuator, and increases the resonant frequency. The silicon nitride thickness is ideally an odd number of quarter wavelengths at a center of the wavelength range, preferably ¾ wavelengths thick. A tunable VCL output 180 (1060 nm tunable emission) is amplified by a semiconductor optical amplifier 190 to create a high power wavelength tunable radiation 195 which can be used for a variety of applications, such as optical coherence tomography and spectroscopy. Tuning of the wavelength is accomplished by adjusting the airgap 150, ideally by applying a voltage between electrodes in the MEMS structure of FIG. 1. A well-designed structure as in FIG. 1 requires a maximum tuning voltage less than about 100V.

The mirror choices of the VCL in FIG. 1 promote wide tuning due to wide mirror bandwidth. Other mirror combinations are possible, such as using a more standard Al(x1)Ga(1−x1)As/Al(x2)Ga(1−x2)As semiconductor mirror with x1 and x2 between 0 and 1, instead of the fully oxidized mirror. Ideally the output suspended mirror is designed to have a reflectivity between 99.0 and 99.9% over the tuning range, and the fixed mirror is >99.9% reflectivity. Another less preferred mirror implementation is a high contrast grating (HCG) for the suspended mirror.

Figure 2:
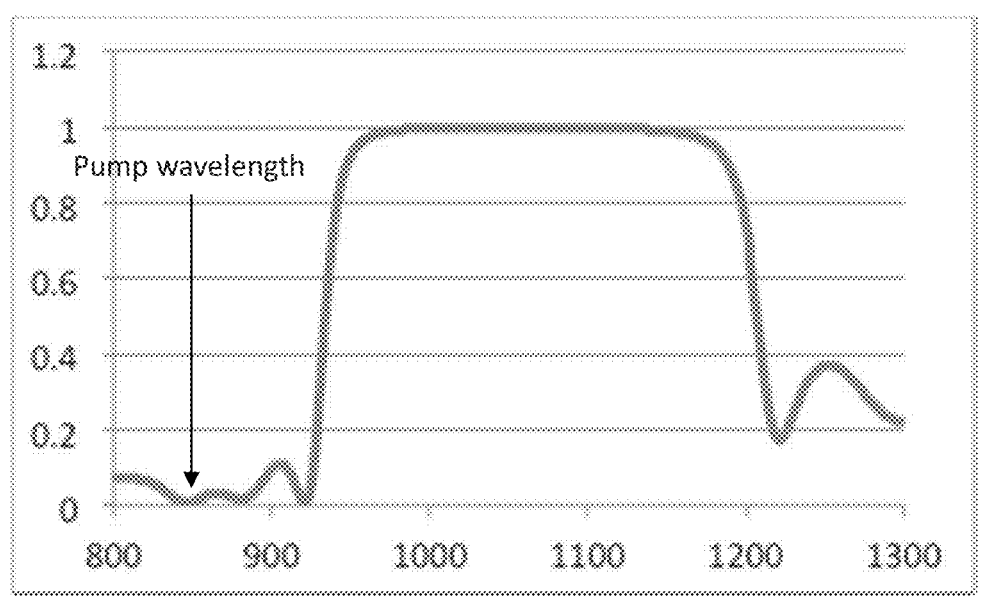
FIG. 2 shows the top mirror spectrum of a MEMS-VCL according to an embodiment.

Efficient optical coupling of the optical pump source 125 to the VCL in FIG. 1 requires that the top dielectric mirror 140 have a spectrum that is transparent at the pump wavelength. An example spectrum is shown in FIG. 2. The mirror design consists of 10.25 periods of a SiO2/Ta2O5 quarter wave stack on a ¾ wavelength SiN membrane, with the top layer being a ⅛ wave layer of SiO2. This ⅛ wave layer flattens the spectrum near the 850 nm pump wavelength.

One necessary requirement of the laser source in FIG. 1 is the separation of pump light from the desired emission in the 950-1150 nm range. This can be accomplished by a WDM coupler as in FIG. 3, where an input fiber 200 brings in the 850 nm pump light to a WDM coupler 220, and an output fiber 210 takes out the tunable 1050 nm emission from the tunable VCL 240. An optical fiber 230 guides both incoming 850 nm pump light to and outgoing 1050 nm VCL emission from the tunable VCL 240 sitting on a GaAs substrate 250. In an alternate separation method in FIG. 4, the VCL 240 is configured to be bottom emitting, and the GaAs substrate 250 absorbs the 850 nm pump radiation while passing only the tunable 1050 nm VCL emission. In yet another embodiment in FIG. 5, the tunable VCL 240 is pumped along an axis different from an optical axis 260 of the tunable VCL.

A number of features of the structure of FIG. 1 promote low-noise single-mode operation. First, use of a single transverse and longitudinal mode pump laser promotes both single transverse mode operation and low relative intensity noise. Careful alignment of the pump beam to a lowest order transverse mode position of the VCL is also critical to ensuring good suppression of higher order transverse modes ideally to better than 45 dB. This suppression is important to maintain long coherence length for SSOCT imaging and avoid spurious image lines. Proper control of the half-symmetric cavity curvature in a range of about 0.5-3 mm with an airgap in a range of about 0.7-1.8 um also promotes single transverse mode operation. Single longitudinal operation is guaranteed by staying away from the edges of the wrap-around point near the edges of a free-spectral range (FSR) of the cavity. FSR is discussed further below and described with the aid of FIG. 9. Ideally the tuning range of the laser should be less than about 95% of the FSR to promote single longitudinal mode operation.

FIG. 1 also shows a metal layer 198 at the back side of a GaAs substrate 175. The metal layer is not needed for electrical contact, but promotes low backside reflection, if the metal is titanium, chromium, or platinum. Low backside reflection is necessary to enable tuning across the tuning range with less than about 1% periodic ripple on the output power spectrum. The ripple is caused by a substrate reflection going in and out of phase with the bottom mirror 130 as the laser is tuned. This ripple is further reduced by lapping the backside of the substrate 175 with a lapping paper or solution with a grit size in a range of about 30 um to about 120 um. Also, reducing the ripple is accomplished by increasing the reflectivity of the GaAs—AlxOy mirror. If the theoretical lossless mirror reflectivity is increased above about 99.95%, substrate reflections become less severe though backside lapping is usually still necessary. The theoretical lossless reflectivity means the calculated reflectivity assuming zero loss in the mirror layers. This reflectivity can be achieved through the use of 6 or more periods of the GaAs—AlxOy mirror. The fully oxidized mirror also promotes operation in a constant polarization state due to the incorporation of anisotropic stress.

A number of additional features of the preferred embodiment in FIG. 1 promote high performance, reliability, and manufacturability. First, the gain region is designed such that the quantum wells have a room temperature photoluminescence (RTPL) peak wavelength that is substantially shorter than a maximum operating wavelength of the laser. For example if the wavelength tuning range of the laser in FIG. 1 is 1000-1100 nm, then the RTPL peak can be as short as 1020 nm. This reduces the required strain in the quantum wells and promotes reliability. The quantum well strain should be in a range of about 1-1.8%. In general, placing the RTPL peak at least 20 nm shorter than a maximum operating wavelength of the laser enhances reliability of the device, and the shorter the PL wavelength, the more reliable the device.

Figure 9:
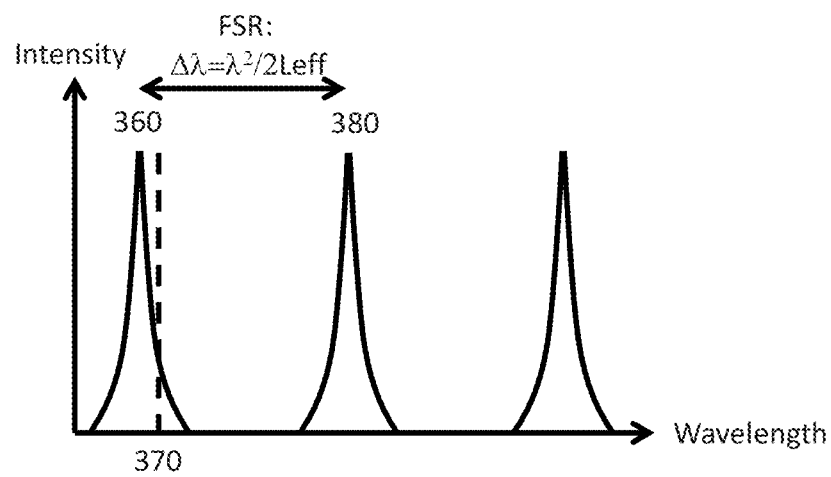
FIG. 9 illustrate the definition of FSR and desired zero bias wavelength.
Figure 11:
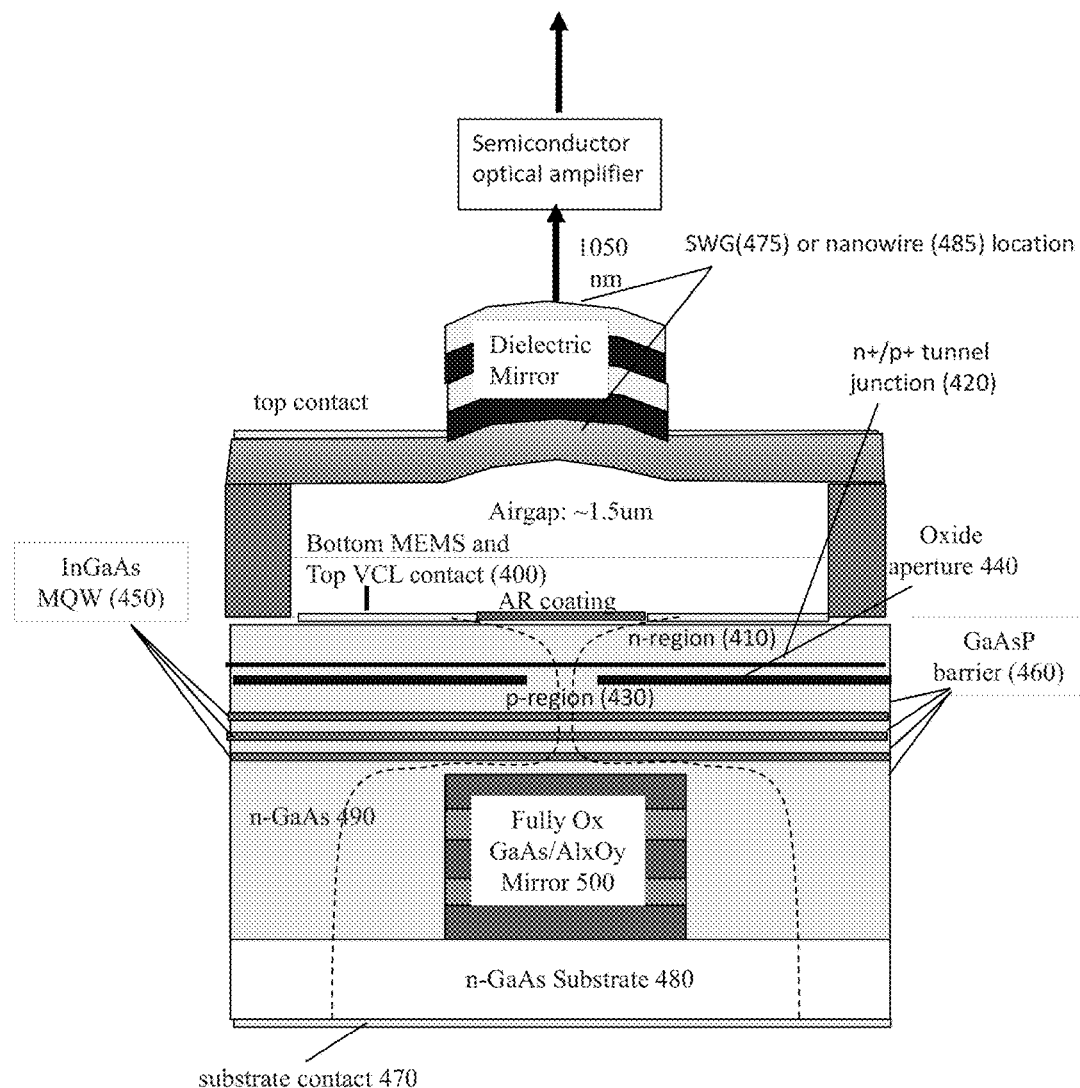
FIG. 11 is a schematic diagram of an electrical pumped MEMS-VCL device according to an embodiment.
Figure 12:
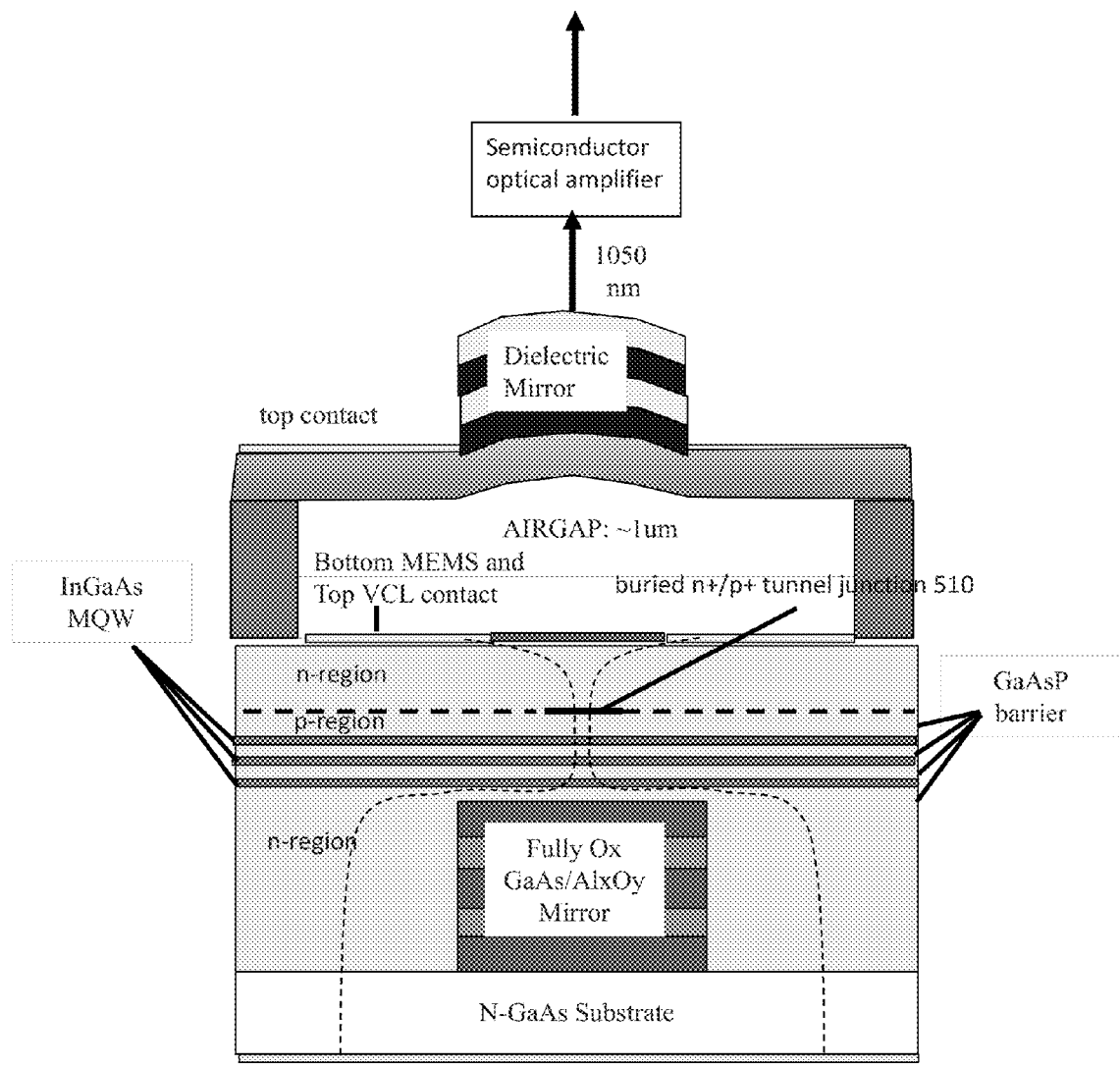
FIG. 12 is a schematic diagram of an electrical pumped MEMS-VCL with buried tunnel junction device according to an embodiment.
Figure 13:
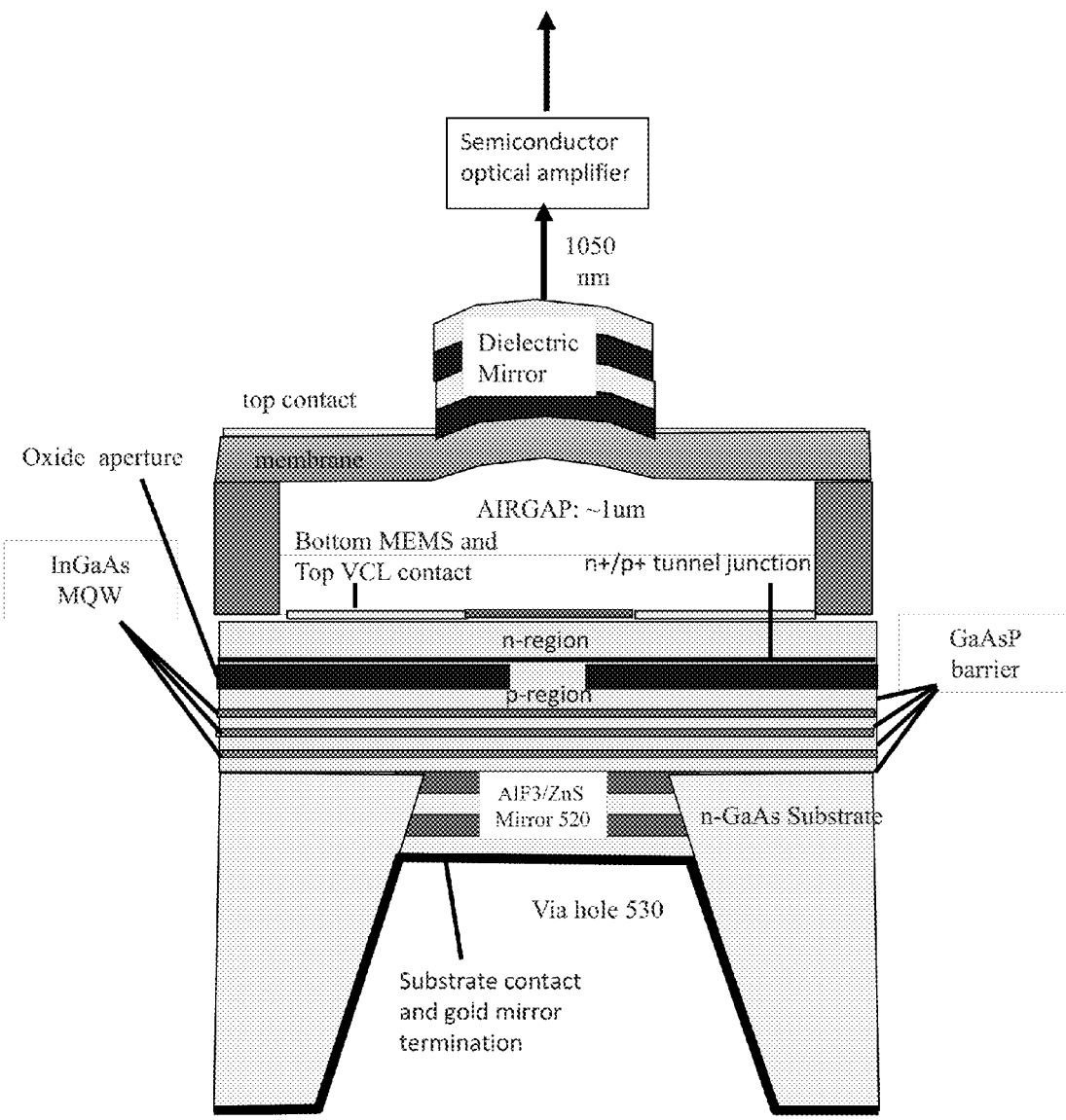
FIG. 13 is a schematic diagram of an electrical pumped MEMS-VCL with evaporated bottom mirror according to another embodiment.

The tuning range of the wavelength swept source shown in FIG. 1, and in subsequent electrically pumped embodiments in FIGS. 11-13, is largely determined by a tuning range of the VCL. The VCL tuning range is maximized by a thin cavity having a large free spectral range (FSR), since the maximum tuning range is the FSR. The FSR is calculated as $\Delta\lambda = \lambda^2/2L_{eff}$, where $L_{eff}$ is the effective cavity length in air, accounting for refractive index and penetration into the mirrors of the device. This is the wavelength spacing between longitudinal cavity modes, as shown in FIG. 9. For use in ophthalmic SSOCT, the FSR is ideally greater than 100 nm for high resolution imaging with ~100 nm tuning range, but FSR exceeding 70 nm or 40 nm can also provide useful devices for lower resolution imaging at for example longer imaging ranges.

Also shown in FIG. 9 is a preferred zero bias wavelength 370, shown in dashes. In a MEMS structure, the ideal position of the zero bias wavelength is to left edge 360 of one FSR, since application of a small bias will cause the mode to tune shorter and wrap around to the longer edge of the FSR at 380. This enables accessing a full FSR in tuning. If the zero bias position 370 were closer to the right edge at 380, then full tuning would be problematic to achieve, since application of voltage in a MEMS structure can generally only shorten the airgap. If the zero-bias wavelength is near the right edge at 380, then prohibitively high voltage would be required to wrap around to the next FSR. Such voltage would likely exceed a snapdown voltage of the device. Note that it is possible through inertial effects to bounce past the zero bias wavelength of the device under dynamic repetitively swept operation, and access wavelengths longer than the zero bias wavelength in this manner. This is not preferable for SS-OCT imaging, however.

Figure 10:
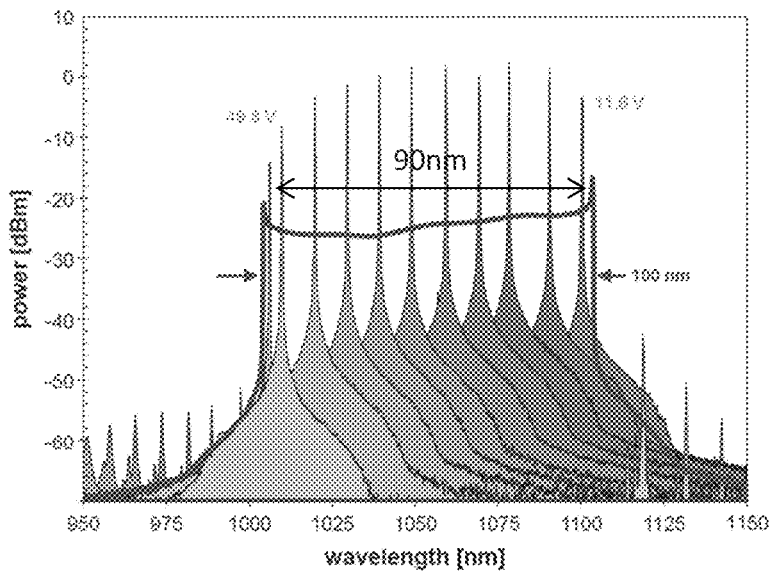
FIG. 10 shows the static and dynamic tuning range of a device according to an embodiment.

Accessing full tuning range also requires proper design of the initial airgap. Since covering one FSR requires a membrane deflection equal to one half a wavelength or about 0.53 um near 1060 nm, and because static deflection of more than ⅓ the total gap is prohibited by snapdown in a MEMS structure, the ideal airgap should exceed 3 half-wavelengths or about 1.6 um. In practice for SSOCT systems, tuning is done under dynamic operation in which it is possible to exceed snapdown. Thus a gap in the range of 2-3 half wavelengths is sufficient to guarantee full tuning under dynamic operation at several hundred kilohertz without snapdown problems. FIG. 10 shows an example of static and dynamic tuning in a 1050 nm VCL, where a 100 nm dynamic tuning range exceeds a 90 nm static tuning range.

Figure 6:
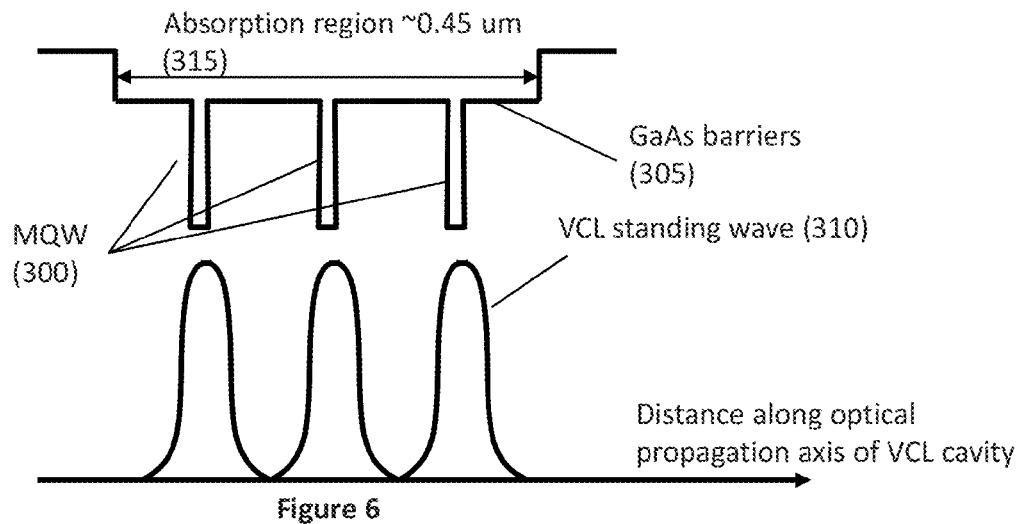
FIG. 6 shows a conduction band and VCL standing wave profile of a device according to an embodiment.
Figure 7:
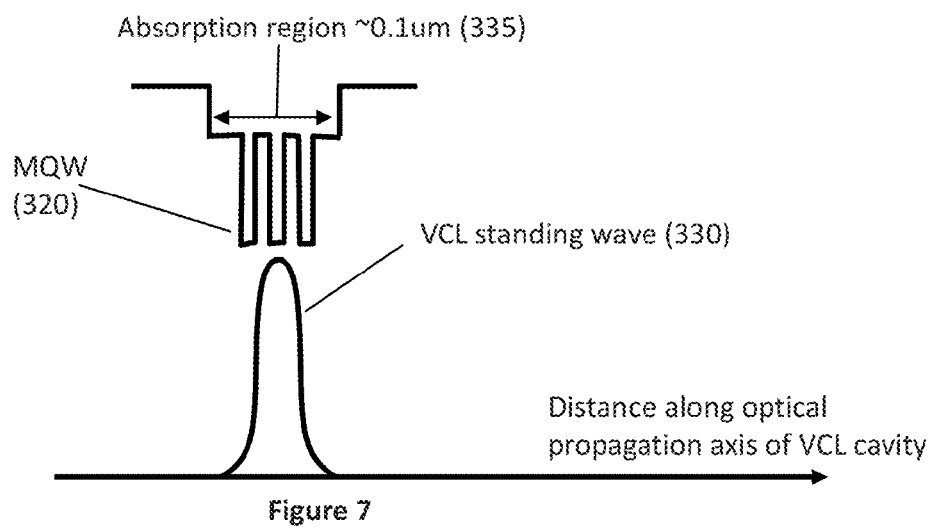
FIG. 7 shows a conduction band and VCL standing wave profile of a device according to another embodiment.
Figure 8:
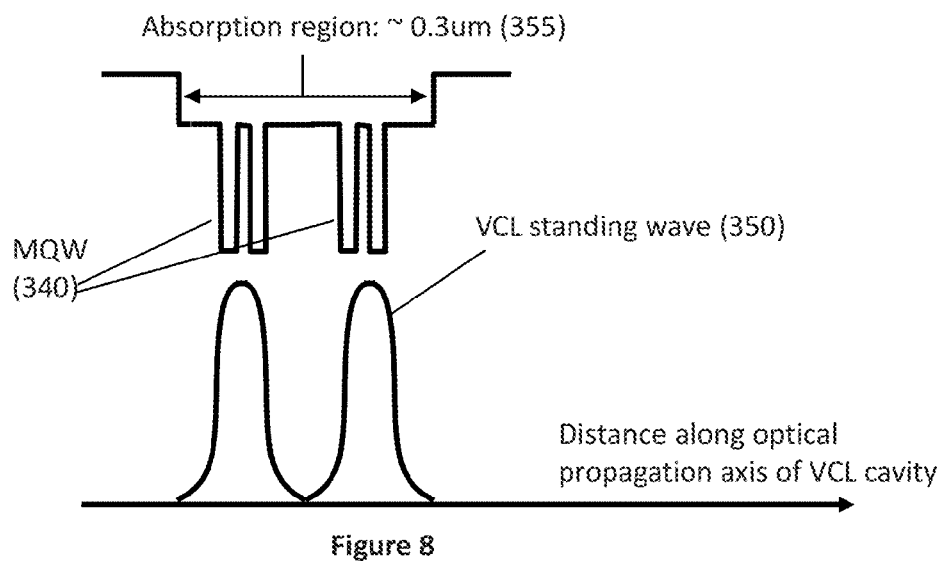
FIG. 8 shows a conduction band and VCL standing wave profile of a device according to another embodiment.

The placement of quantum wells inside the cavity, relative to an optical standing wave in the laser cavity also promotes performance and reliability. FIGS. 6-8 illustrate 3 preferred designs for quantum well placement in the structure of FIG. 1. The horizontal axis in these figures is distance along an optical propagation axis of the VCL cavity. The top of each figure represents the conduction band of material in the structure illustrating quantum well and absorber locations. The bottom of each figure represents a standing wave of intra-cavity radiation in each structure. In FIG. 6, three quantum wells of a multi-quantum well region 300 are aligned with 3 separate maxima of a standing wave pattern 310 of the optical cavity. In this periodic gain structure, gain is not only enhanced relative to quantum well placement away from standing wave peaks, but the wells are sufficiently separated that they are de-coupled with respect to strain accumulation. This means that the total strain thickness product of the quantum wells can exceed the normal strain-thickness product limit of 200 Angstrom-percent. Also shown is an absorption region 315 with thickness of about 0.45 microns, which leads to absorption of more than 40% of the 850 nm pump power. Most of the absorption occurs in the GaAs barriers 305 of the quantum wells, and only a minority of the absorption happens in the wells. All photogenerated electrons and holes diffuse into the quantum wells 300, so absorbed pump light is efficiently converted to tunable VCL light.

Another preferred MQW embodiment is shown by FIG. 7. Here, all three quantum wells of a MQW region 320 are aligned with a single standing wave peak of a standing wave pattern 330 inside the VCL optical cavity. In this case tensile-strained GaAsP strain-compensated barriers are provided to compensate the compressively strained InGaAs quantum wells. The advantage of FIG. 7 is that the cavity thickness can be reduced, leading to a larger cavity free spectral range and wider tuning. The disadvantage is a reduced thickness absorption region 335, having about 0.1 um thickness, causing an increase in required pump power. Here significant absorption happens in both wells and barriers of the structure.

A third preferred placement is shown in FIG. 8, where 2 sets of 2 quantum wells in an MQW region 340 are aligned with 2 standing wave peaks of an optical standing wave pattern 350. Here an absorber 355 of thickness around 0.3 um is employed, leading to a compromise between pump absorption and wide free spectral range. This structure also employs tensile-strained GaAsP barriers.

Reliable operation of the VCL shown in FIG. 1 is also promoted by limiting a pump power presented to the VCL. An absorbed power of 0.3 to 30 mW is preferable to maintain reliable operation, and an absorbed pump power less than about 15 mW is ideal.

FIG. 11 illustrates another preferred embodiment of a wavelength-swept source according to the present invention. In this figure electrons and holes are provided to the gain region through an electrical pump current instead of an optical pump. A bottom MEMs contact 400 also serves as the top contact for injection of current into the quantum wells. The contact 400 injects electrons into an n-region 410, which are converted to holes in a p-type region 430 through an n+/p+ tunnel junction 420, which is preferably n+GaAs/p+GaAs. Contact to the n-layer 410 enables efficient lateral spreading of the current and promotes single-mode operation. The p-type region 430 contains a current constriction oxide aperture 440 which is formed by lateral oxidation of AlGaAs. Carriers are injected from the region 430 through the current aperture 440 into the gain region comprised of an InGaAs multiquantum well (MQW) 450 with GaAsP barriers 460. Oppositely charged carriers are injected into the MQW from a substrate contact 470 through the GaAs substrate 480 and GaAs cladding 490, around a fully oxidized mirror 500 comprising insulating AlxOy layers. In this structure, the tunnel junction 420 is preferably placed at a node in the optical standing wave pattern inside the cavity, to reduce sensitivity to free carrier losses in the highly doped region. In addition, placement of the oxide aperture 440 near a node promotes single-mode operation, as it reduces the waveguide confinement of the oxide.

Polarization control of this structure is partially provided by anisotropic stress of the fully oxidized mirror, but further polarization selection can be provided by incorporation of one or more nanowires 485 or a sub-wavelength grating 475 at the top or bottom of the of the suspended DBR. These approaches can also be employed in optically pumped structures such as in FIG. 1. In an electrically pumped structure, previous workers have employed asymmetric current injection in fixed wavelength structures, which can also be employed in electrically pumped tunable VCLs here.

An alternate preferred electrically pumped embodiment is shown in FIG. 12, in which constriction is provided by a buried tunnel junction 510 of limited lateral extent instead of the oxide aperture 440 in FIG. 11. The buried tunnel junction has the advantage of being lithographically defined and therefore more controllable than the oxide aperture 440, the latter defined by oxidation time and temperature, but has the disadvantage of requiring a regrowth step to bury the tunnel junction. Ideally, the buried tunnel junction 510 is aligned with a standing wave node to minimize free carrier losses.

FIG. 13 shows a third preferred embodiment of an electrically pumped VCL, in which the fully oxidized mirror 500 is replaced by an evaporated mirror 520 evaporated through a substrate via hole 530. A preferred embodiment of the evaporated mirror is a quarter wave stack of aluminum fluoride and Zinc Sulfide, terminated by a metal layer such as gold. Other high index contrast wide bandwidth evaporated stacks include other fluorine compounds such as magnesium fluoride as the low index layer.

Figure 14:
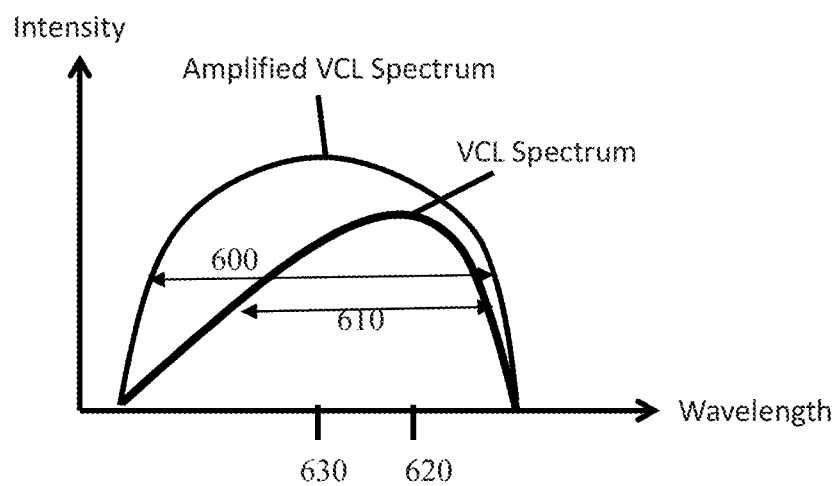
FIG. 14 shows the pre and post-amplified VCL spectra of a device according to an embodiment.

The electrically and optically pumped embodiments shown in FIGS. 1, 11-13 all include a semiconductor optical amplifier (SOA) to amplify a tunable radiation emitted by the VCL. The SOA is not required for all applications, but is desired in most swept source OCT applications which require high average power across the wavelength range. The design of this SOA is critical to performance, reliability and manufacturability. FIG. 14 illustrates how SOA gain saturation can provide an improved full-width half maximum (FWHM) 600 of post-amplified VCL radiation, relative to a FWHM 610 of pre-amplified VCL emission. The peak wavelength of the spectrum is also shifted from a pre-amplified peak wavelength 620 to a post-amplified peak wavelength 630. This shift can also be advantageous for many applications.

Figure 15:
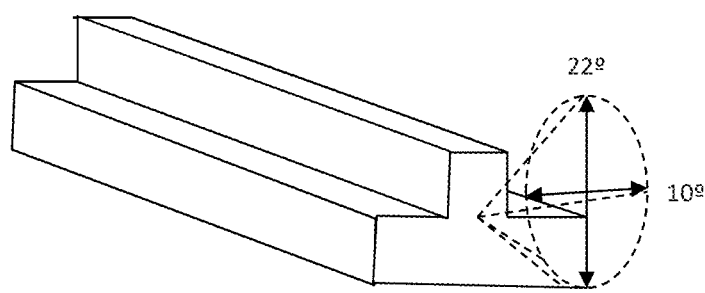
FIG. 15 shows a ridge waveguide semiconductor optical amplifier device according to an embodiment.

The preferred SOA uses compressively strained InGaAs quantum wells with a strain level in a range of about 1-1.8%. The preferred SOA is also polarization sensitive, amplifying only one polarization. An alternate less preferred implementation uses an InGaAs quantum dot amplifier. One preferred design uses a ridge waveguide design with 2 InGaAs quantum wells with tensile strained GaAsP barriers in a waveguide having a FWHM vertical beam divergence less than 25 degrees, as shown in the example divergence angles of FIG. 15. The divergence angle is defined as the angle of the amplified spontaneous emission emitted by the amplifier when operated as a superluminescent diode. Low divergence angle improves fiber-coupling efficiency and chip-to-chip gain of the SOA. The gain is also aided by the use of 2 quantum wells. For some applications, a single quantum well can be employed providing less gain, and with one quantum well strain compensation is not necessary. In all strained QW SOAs using InGaAs, the preferred well width is in a range of 5-10 nm. Reliability is improved by thinner quantum wells, but a second quantum state appearing in the well in a width range of about 8-10 nm improves gain bandwidth. Reliability is also improved by minimizing a room temperature photoluminescence (RTPL) wavelength of the quantum wells, with a range of about 1050-1085 nm desirable for good reliability and high gain in a wavelength range from around 980 nm to around 1120 nm.

Another factor in InGaAs quantum well SOA design is providing high gain without sacrificing reliability. This requires operating in the proper regime of device length and operating current. Ideally the device length should be between about 1.2 mm and about 2.0 mm, and the drive current should be between about 200 mA and about 700 mA. This enables output powers of 10-30 mW with input powers of 0.3-3 mW.

Another consideration in the design of the wavelength swept sources in FIGS. 1, 11-13 above is the speed of tuning A number of design choices enhance tuning speed in a MEMS tunable structure. One is the use of stress in the SiN membrane 170. Tensile stresses of >100 MPascal are preferred, and give a mechanical resonance that is substantially increased relative to a zero-stress film. Tensile stress>400 Mpa lead to very high resonances approaching 500 kHz and higher depending on the geometry. Compressive stress could also be employed, but tensile stress enables better wavelength control. Stressed membranes also enable control of zero bias wavelength through the amount of sacrificial layer undercutting. The zero bias wavelength is a function of the amount of sacrificial undercut, which enables zero-bias wavelength adjustment during fabrication. Combining increased stress with small geometries can increase the MEMS mechanical resonance beyond 1 MHz. Important resonance regimes are 10 kHz, 100 kHz, 200 kHz, 400 kHz, and 1 MHz. All of these can be achieved by control of geometry and stress. The structure of FIG. 1 illustrates 3 supporting arms, but 2, 4, or 8 are desirable numbers of supporting arms for various applications. The basic geometry of a central plate with multiple supporting arms can be changed to a perforated diaphragm in the limit where the arm length goes to zero and perforations are introduced in the central plate.

In addition to mechanical resonance, the frequency response of the MEMS structure can be flattened by using squeeze-film damping introduced by viscous air. This can be controlled by adjustment of background gas or pressure, and by control of the central plate and arm areas. In general, increased pressure, heavier gases, and wider arms/plates increase damping and flatten frequency response. Using these parameters, near critically damped operation can be achieved. In some applications, highly underdamped resonant operation in vacuum is desirable as this reduces required voltage to typically less than 10V for full tuning Vacuum environments can be provided by evacuated butterfly or transistor outline (TO) packages.

Figure 16:
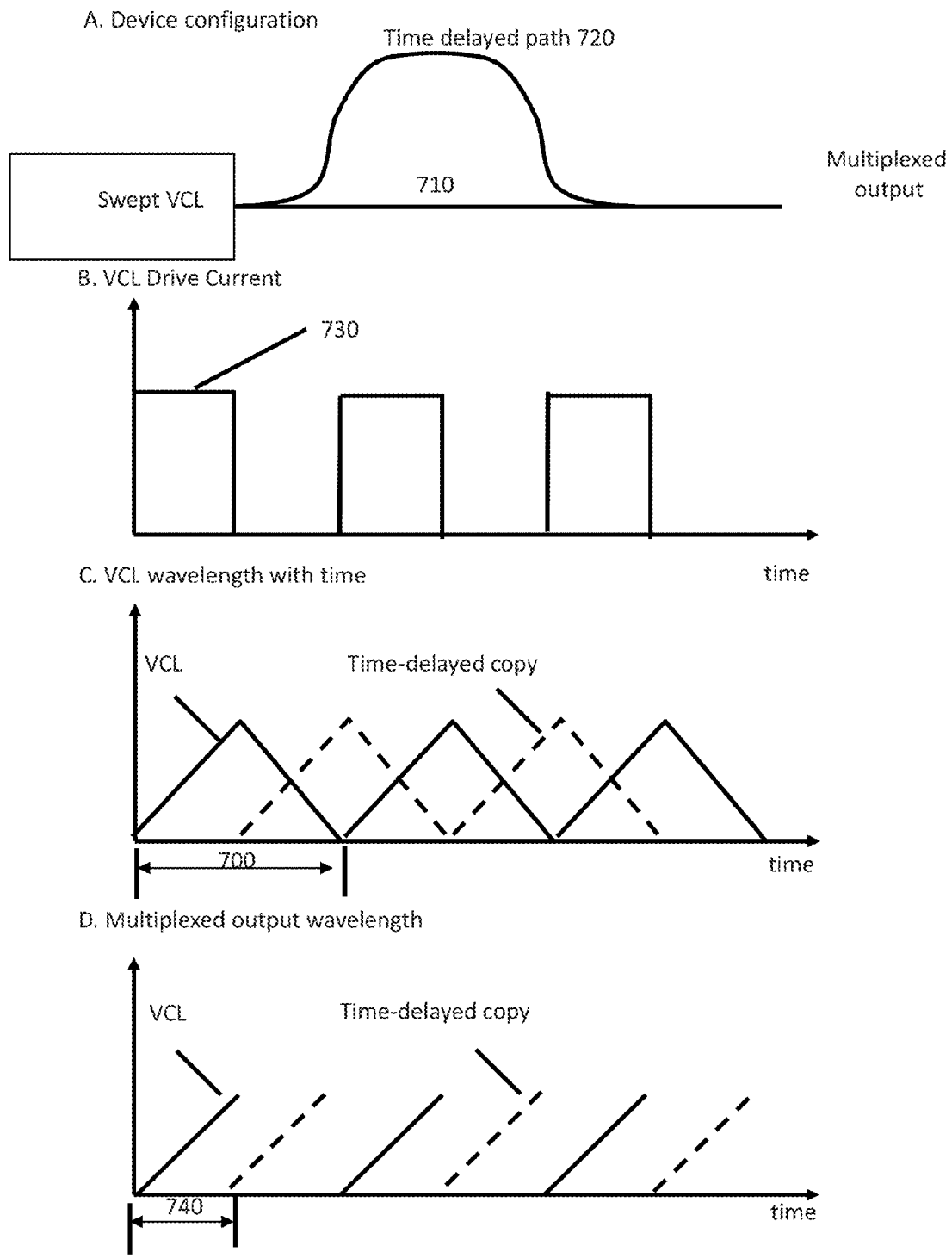
FIG. 16 shows the configuration of a device, the drive current, wavelength trajectory and multiplexed output versus time according to an embodiment.

The speed of the optically and electrically pumped swept sources in FIGS. 1, 11-13 can also be increased by incorporation of one or more delay lines and multiplexing of time delayed outputs. An example of this for one delay line which doubles sweep rate is shown in FIG. 16. An electrically pumped VCL output with a first wavelength repetition period 700 shown in FIG. 16C is split to a first optical path 710 and a second time-delayed optical path 720, the path 720 delayed half a repetition period, as shown in FIG. 16A. The wavelength is scanned bi-directionally, as shown in FIG. 16C, but the VCSEL is turned off during the backward sweep by turning off drive current 730 as shown in FIG. 16B. The multiplexed output containing both the VCL output and delayed output is shown in FIG. 16D. The copy is inserted during the blanked backward sweep, resulting in a final unidirectional scan with a repetition period 740 that is half the repetition period 700 (twice the repetition frequency), with nearly 100% duty cycle. The technique of FIG. 16 can be extended to N delay lines with the final multiplexed sweep having a repetition frequency that is N times the repetition frequency of the original VCL sweep.

The wavelength swept light source described here has application in swept source OCT (SSOCT) imaging of the human eye. The single mode operation guarantees long coherence length exceeding 100 mm, enabling whole eye imaging including both the anterior eye and retinal layers.

Though the invention described here has been focused on the 950-1150 nm window, many of the design principles presented can be applied to other wavelength regimes. In addition, many design principles described with respect to electrically pumped devices can be applied to optically pumped devices and vice versa. While this invention has been particularly shown and described with references to preferred and alternate embodiments thereof, it will be understood by those skilled in the art that various changes in form and details may be made therein without departing from the spirit and scope of the invention as defined by the appended claims.

What is claimed is:

1. A wavelength-tunable light source operative to emit wavelength tunable radiation over a wavelength range contained in a wavelength span between about 950 nm and about 1150 nm, said wavelength tunable light source comprising a vertical cavity laser (VCL), said VCL having a gain region with at least one compressively strained quantum well containing Indium, Gallium, and Arsenic, said vertical cavity laser further comprising a first portion including a first mirror, a second portion including a second mirror attached to a mechanical structure including a flexible membrane with a support structure, an adjustable airgap between said second portion and said first portion, a first means for injecting electrons and holes into said gain region, a second means for adjusting said airgap, and a third means for obtaining substantially single longitudinal and transverse mode operation over said wavelength tuning range, wherein a peak room-temperature photoluminescence wavelength of said gain region is more than about 50 nm shorter than a maximum operating wavelength of said tunable laser.

2. The wavelength tunable light source of claim 1, wherein a peak room-temperature photoluminescence wavelength of said gain region is more than about 70 nm shorter than a maximum operating wavelength of said tunable laser.

3. The wavelength tunable light source of claim 1, wherein said first mirror comprises an alternating stack including a first $Al(x1)Ga(1-x1)As$ layer and a second $Al(x2)Ga(1-x2)As$ layer, where x1 and x2 are in a range of 0-1.

4. The wavelength tunable light source of claim 1, where said first mirror comprises an alternating stack including a first material containing aluminum and oxygen, and a second material that is $Al(x)Ga(1-x)As$, where x is in a range of 0-1.

5. A wavelength-tunable light source operative to emit wavelength tunable radiation over a wavelength range contained in a wavelength span between about 950 nm and about 1150 nm, said wavelength tunable light source comprising a vertical cavity laser (VCL), said VCL having a VCL gain region with at least one compressively strained quantum well containing Indium, Gallium, and Arsenic, said vertical cavity laser further comprising a first portion including a first mirror, a second portion including a second mirror attached to a mechanical structure including a flexible membrane with a support structure, an adjustable airgap between said second portion and said first portion, a first means for injecting electrons and holes into said gain region, a second means for adjusting said airgap, a third means for obtaining substantially single longitudinal and transverse mode operation over said wavelength tuning range, said wavelength-tunable light source further comprising a semiconductor optical amplifier (SOA) comprising at least one SOA quantum well including Indium, Gallium, and Arsenic, said at least one SOA quantum well having a room temperature photoluminescence wavelength in a range of about 1050 nm-1085 nm, wherein a peak room-temperature photoluminescence wavelength of said gain region is more than about 50 nm shorter than a maximum operating wavelength of said tunable laser.

6. The wavelength tunable light source of claim 5, wherein said semiconductor optical amplifier includes exactly one compressively strained SOA quantum well comprising Indium, Gallium, and Arsenic.

7. The wavelength tunable light source of claim 5, wherein said semiconductor optical amplifier contains exactly 2 SOA quantum wells with at least one tensile-strained barrier.

8. The wavelength tunable light source of claim 5, wherein said at least one SOA quantum well comprises two confined quantum states.

9. The wavelength tunable light source of claim 5, wherein a vertical beam divergence of said semiconductor optical amplifier is less than about 25 degrees full-width at half-maximum.

10. The wavelength tunable light source of claim 5, wherein said first mirror comprises an alternating stack including a first $Al(x1)Ga(1-x1)As$ layer and a second $Al(x2)Ga(1-x2)As$ layer, where x1 and x2 are in a range of 0-1.

11. The wavelength tunable light source of claim 5, wherein said first mirror comprises an alternating stack comprising including a first material containing aluminum and oxygen, and a second material that is $Al(x)Ga(1-x)As$, where x is in a range of 0-1.

12. A wavelength-tunable light source operative to emit wavelength tunable radiation over a wavelength range contained in a wavelength span between about 950 nm and about 1150 nm, said wavelength tunable light source comprising a vertical cavity laser (VCL), said VCL having a gain region with at least one compressively strained quantum well containing Indium, Gallium, and Arsenic, said vertical cavity laser further comprising a first portion including a first mirror, a second portion including a second mirror attached to a mechanical structure including a flexible membrane with a support structure, an adjustable airgap between said second portion and said first portion, a first means for injecting electrons and holes into said gain region, a second means for adjusting said airgap, wherein said vertical cavity laser is surrounded by a vacuum environment which enables a substantially under-damped mechanical resonance of said mechanical structure, wherein a peak room-temperature photoluminescence wavelength of said gain region is more than about 50 nm shorter than a maximum operating wavelength of said tunable laser.

13. The wavelength tunable light source of claim 12, wherein said vacuum environment is provided by an evacuated butterfly package.

14. The wavelength tunable light source of claim 12, wherein said vacuum environment is provided by an evacuated transistor outline (TO) package.

15. The wavelength tunable light source of claim 12, wherein said wavelength range is repetitively scanned at a mechanical resonant frequency of said mechanical structure.

16. The wavelength tunable light source of claim 12, wherein said wavelength range is covered with a maximum voltage less than about 10V.

17. The wavelength tunable light source of claim 1, wherein said VCL is driven by a periodic tuning waveform periodically adjusting said airgap, such that said wavelength tunable radiation has a periodic wavelength variation with time at a first wavelength repetition frequency and a first repetition period, further comprising at least one optical delay line for generating at least one time-delayed copy of said wavelength tunable radiation, a combiner for combining all of said time-delayed copies into a common optical path to create a multiplexed wavelength-swept radiation, and a fifth means for turning off said VCL during a time window of said first wavelength repetition period, wherein said multiplexed wavelength swept radiation has a second wavelength repetition frequency which is an integer multiple of said first wavelength repetition frequency.

18. A system for optical coherence tomography, the system comprising at least one wavelength tunable light source of claim 1, wherein said VCL is driven by a periodic tuning waveform which periodically adjusts said airgap such that said wavelength-tunable radiation is repetitively tuned over said wavelength range, a splitter for splitting said wavelength tunable radiation to a sample and a reference path, an optical detector for detecting an interference signal between a reflection from said sample and light traversing said reference path, and a signal processing system for constructing an image from said interference signal.

19. The system of claim 18, wherein said sample is an in-vivo human eye.

20. The system of claim 19, wherein said image includes a portion of both the anterior eye and the retina.

21. The system of claim 18, wherein a dynamic coherence length of said wavelength-swept radiation exceeds 100 mm.

22. A system for optical coherence tomography, the system comprising at least one wavelength tunable light source of claim 5, wherein said VCL is driven by a periodic tuning waveform which periodically adjusts said airgap such that said wavelength-tunable radiation is repetitively tuned over said wavelength range, a splitter for splitting said wavelength tunable radiation to a sample and a reference path, an optical detector for detecting an interference signal between a reflection from said sample and light traversing said reference path, and a signal processing system for constructing an image from said interference signal.

23. The system of claim 22, wherein said sample is an in-vivo human eye.

24. The system of claim 23, wherein said image includes a portion of both the anterior eye and the retina.

25. The system of claim 22, wherein a dynamic coherence length of said wavelength-swept radiation exceeds 100 mm.

26. A system for optical coherence tomography, the system comprising at least one wavelength tunable light source of claim 12, wherein said VCL is driven by a periodic tuning waveform which periodically adjusts said airgap such that said wavelength-tunable radiation is repetitively tuned over said wavelength range, a splitter for splitting said wavelength tunable radiation to a sample and a reference path, an optical detector for detecting an interference signal between a reflection from said sample and light traversing said reference path, and a signal processing system for constructing an image from said interference signal.

27. The system of claim 26, wherein said sample is an in-vivo human eye.

28. The system of claim 27, wherein said image includes a portion of both the anterior eye and the retina.

29. The system of claim 26, wherein a dynamic coherence length of said wavelength-swept radiation exceeds 100 mm.

30. The wavelength tunable light source of claim 5, wherein a thickness of said at least one SOA quantum well is in a range of about 5-10 nm.

* * * * *